(12) United States Patent
Moore

(10) Patent No.: US 10,723,548 B2
(45) Date of Patent: Jul. 28, 2020

(54) HYGIENIC INTERACTIVE SYSTEM FOR SANITARY MATERIAL

(71) Applicant: Shacorri Moore, Atlanta, GA (US)

(72) Inventor: Shacorri Moore, Atlanta, GA (US)

(*) Notice: Subject to any disclaimer, the term of this patent is extended or adjusted under 35 U.S.C. 154(b) by 50 days.

(21) Appl. No.: 15/948,996

(22) Filed: Apr. 9, 2018

(65) Prior Publication Data
US 2018/0327181 A1    Nov. 15, 2018

Related U.S. Application Data

(60) Provisional application No. 62/482,853, filed on Apr. 7, 2017.

(51) Int. Cl.
| | | |
|---|---|---|
| *F23N 5/22* | (2006.01) | |
| *B65F 1/00* | (2006.01) | |
| *A61F 13/551* | (2006.01) | |
| *A61F 13/472* | (2006.01) | |
| *B65F 1/14* | (2006.01) | |
| *B65F 1/06* | (2006.01) | |
| *A61F 13/84* | (2006.01) | |
| *B65F 1/16* | (2006.01) | |
| *A61F 13/15* | (2006.01) | |
| *B65F 1/10* | (2006.01) | |

(52) U.S. Cl.
CPC ............ *B65F 1/004* (2013.01); *A61F 13/472* (2013.01); *A61F 13/5516* (2013.01); *B65F 1/0026* (2013.01); *B65F 1/06* (2013.01); *B65F 1/1415* (2013.01); *A61F 13/15252* (2013.01); *A61F 13/8405* (2013.01); *A61F 2013/47281* (2013.01); *B65F 1/10* (2013.01); *B65F 1/16* (2013.01); *B65F 2210/129* (2013.01); *B65F 2210/168* (2013.01); *B65F 2240/164* (2013.01)

(58) Field of Classification Search
CPC . F23G 2200/00; B02C 19/0075; A61F 13/472
See application file for complete search history.

(56) References Cited

U.S. PATENT DOCUMENTS

| | | | | |
|---|---|---|---|---|
| 3,467,035 A | * | 9/1969 | Anderson | F23G 5/14 |
| | | | | 110/210 |
| 5,444,984 A | * | 8/1995 | Carson | A47B 81/00 |
| | | | | 62/3.4 |
| 6,739,114 B2 | | 5/2004 | Shaffer | |
| 7,490,731 B2 | | 2/2009 | Hautop | |
| 8,215,089 B2 | | 6/2012 | Stravitz | |
| 9,033,176 B2 | | 5/2015 | Liistro et al. | |
| 2005/0113970 A1 | * | 5/2005 | Holmes | A47B 88/00 |
| | | | | 700/242 |
| 2007/0045324 A1 | | 3/2007 | Mitchell | |

(Continued)

FOREIGN PATENT DOCUMENTS

EP    1079783 A4    3/2001

*Primary Examiner* — Jason Lau

(57) ABSTRACT

The present invention relates to a hygienic interactive system for sanitary material comprising a dispenser having at least three drawers, at least three buttons corresponding to the aforementioned three drawers, and a display screen; and, a disposal feature having at least two compartments and at least one sensor located on the top compartment The sensor being connected with the display screen and with drawers of the dispenser. The disposal additionally comprises at least three compartments containing an incinerating compartment.

12 Claims, 6 Drawing Sheets

(56) References Cited

U.S. PATENT DOCUMENTS

2014/0000226 A1    1/2014  Staab
2014/0225485 A1*   8/2014  Freimuth ............... B25H 3/006
                                                      312/122

* cited by examiner

HYGIENIC INTERACTIVE SYSTEM FOR SANITARY MATERIAL

CROSS-REFERENCE TO RELATED APPLICATIONS

The present application claims priority to provisional U.S. patent application Ser. No. 62/482,853, filed Apr. 7, 2017, entitled "Hygienic Interactive System For Sanitary Material," the disclosure of which is incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

FIELD OF INVENTION

The invention relates to hygienic interactive system for sanitary material

BACKGROUND OF THE INVENTION

The average age of women when begin their menstrual cycle is about 12.5 years, typically menorrhea lasts till a woman is between 48-50 years of age. Being a large part of a woman's life and lasting through the most productive and fertile years it presses the imminent need for advanced technology in this field. Currently there are multiple options for sanitary material dispensers available, there are also a few options for disposers. However, an advanced and compact system to serve the purpose of disposing while dispensing sanitary material for personal and public use is not currently available. The absence of such a unit results in great inconvenience. Most often women find themselves in embarrassing situations, by not knowing where to dispose the used sanitary material, especially in a unfamiliar environment (another's home or a public place). Many are too shy to step out of the toilet cabin and dispose it in the common trash cans; others are too lazy. In both scenarios many such sanitary materials end up being flushed down toilets and clogging the sewage system. Even if the sanitary material does reach the trash can, there is yet another problem of how the waste is disposed, often it is dumped in a landfill, where it may be left exposed presenting biohazard and due to the shear bulk of hygienic products consumed daily present a serious threat for the ecosystem. A further problem is that many women do not always carry a spare sanitary material with them. Therefore, when a menstrual flow starts unexpectedly or when the used sanitary material is due for dispose, the woman postpones the action until the new napkin is finally available to her. This may cause multiple problems, either she is she is not able to locate a sanitary material in a timely manner or the older material becomes overused, resulting in stress, potential infections or simply an unhygienic state of being.

Therefore, the current problems with sanitary waste disposal and material handling include as least the following: improper waste handling by users and disposers, inefficient waste disposal in terms of waste segregation, unhygienic sanitary material storage and under advanced sanitary material dispensing. Current technologies offer either disposal systems or dispensing systems as seen in U.S. Pat. No. 9,033,176 B2, which relates to a waste disposal apparatus for discreet and hygienic disposal of used bodily waste products, such as tampons, pads, liners, briefs, condoms, wipes etc. An advanced combination of an interactive and multifunctional system dedicated to disposal and dispensing of sanitary waste for women's hygiene is not available. Disposing machines although available by technology, have not been widely used due to the lack of practicality. Such units are neither aesthetically preferred in toilets nor are they compact and easy to be used directly by the women at the time of disposing.

For a phenomenon so widely existing and so essential to the fertility of women, an advanced technology is greatly demanded. Thus, there is a need for an urgent advances in this field that can address the problems posed above collectively.

SUMMARY OF THE INVENTION

An object of the present invention is a hygienic interactive system for sanitary material comprising a dispenser; and, a disposal.

A further object of the present invention is a hygienic interactive system for sanitary material further comprising a dispenser; and, a disposal; wherein the disposal comprises an incinerator.

An even further object of the present invention is a hygienic interactive system for sanitary material further comprising at least one sensor, wherein the at least one sensor detects a disposed waste item and offers a suitable sanitary material for dispensing.

BRIEF DESCRIPTION OF DRAWINGS

The advantages and features of the present invention will be better understood as the following description is read in conjunction with the accompanying drawings, wherein:
1=Lid
2=securing cap
3=display screen
4=buttons (A, B, C)
5=L1
6=L2
7=L3
8 (FIG. 2)=sanitary waste
9=odorant; disinfectant
10=opening flap
11=fume absorbent material
12=electric mesh
13=incinerated waste
14=waste disposal bag/tube
15=A (drawer)
16=B (drawer)
17=C (drawer)
18=sensor FIG. 1A Front view of the outer body of the invention The system is shown with the lid open. The three components of the second mode of the system are shown. The incinerating compartment is marked as L2.

DETAILED DESCRIPTION OF THE INVENTION

Figure 1A:
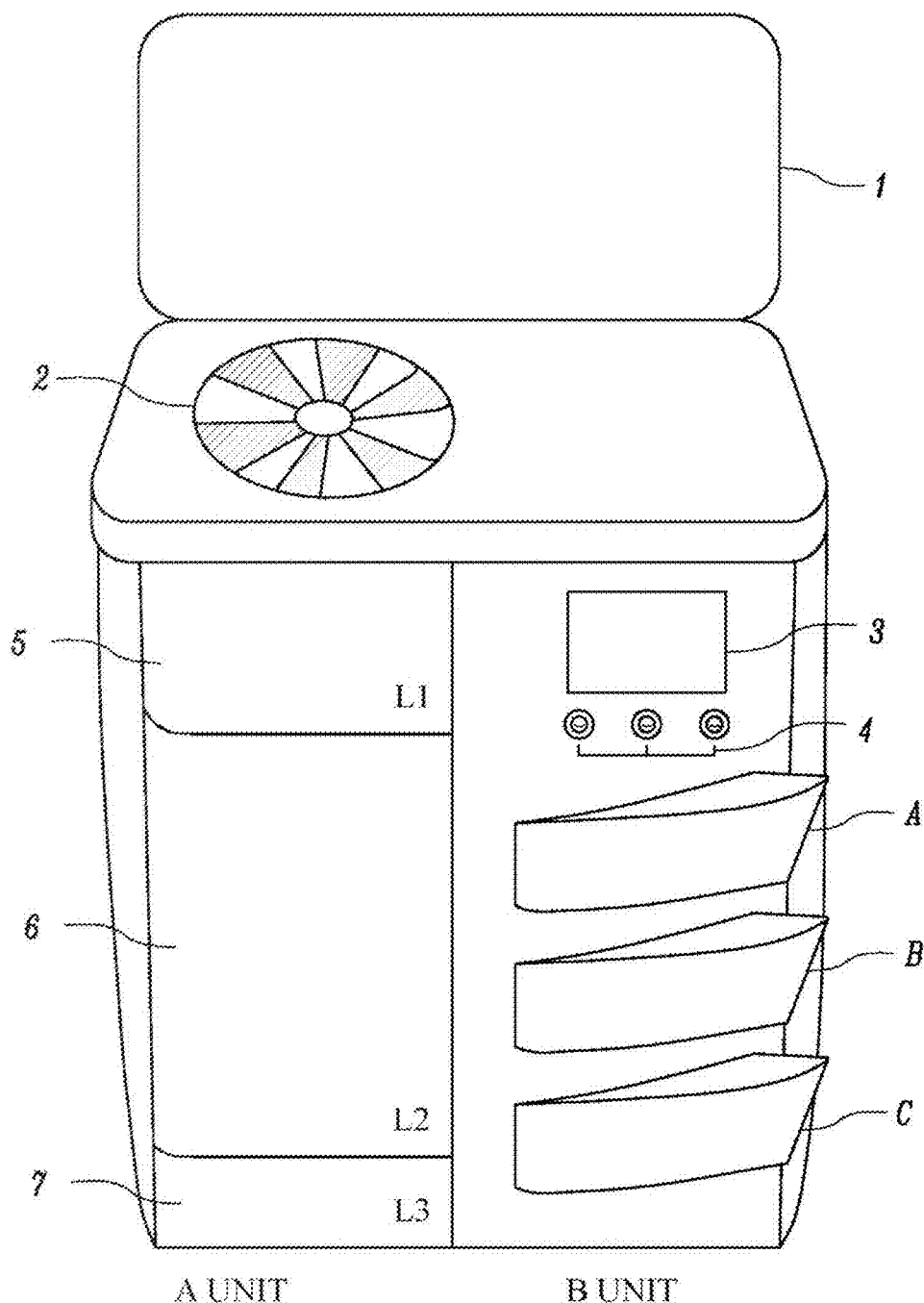
FIG. 1B: The internal mechanism of only the disposal unit (Unit A) of the system.
Figure 1B:
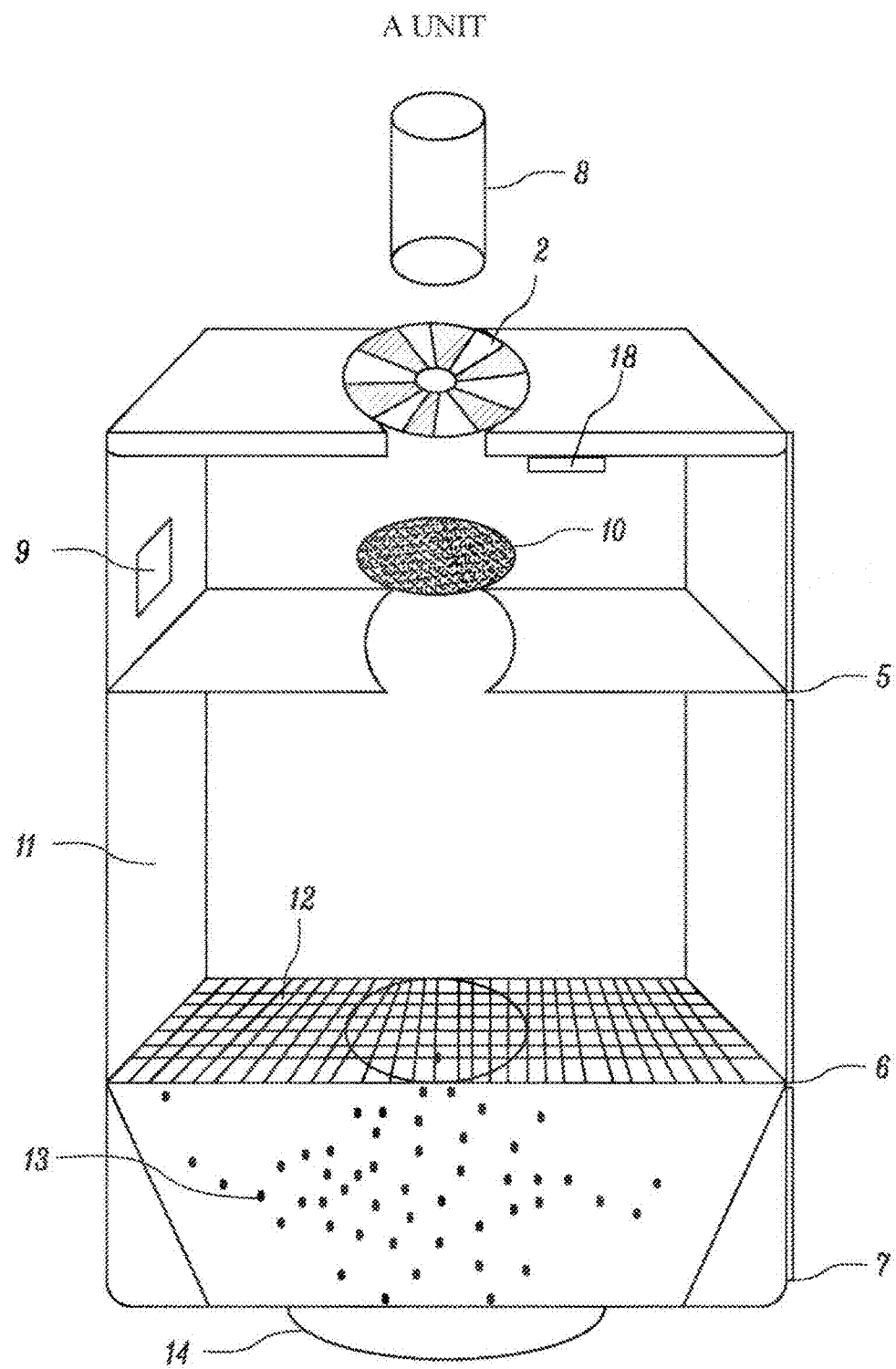
Figure 2:
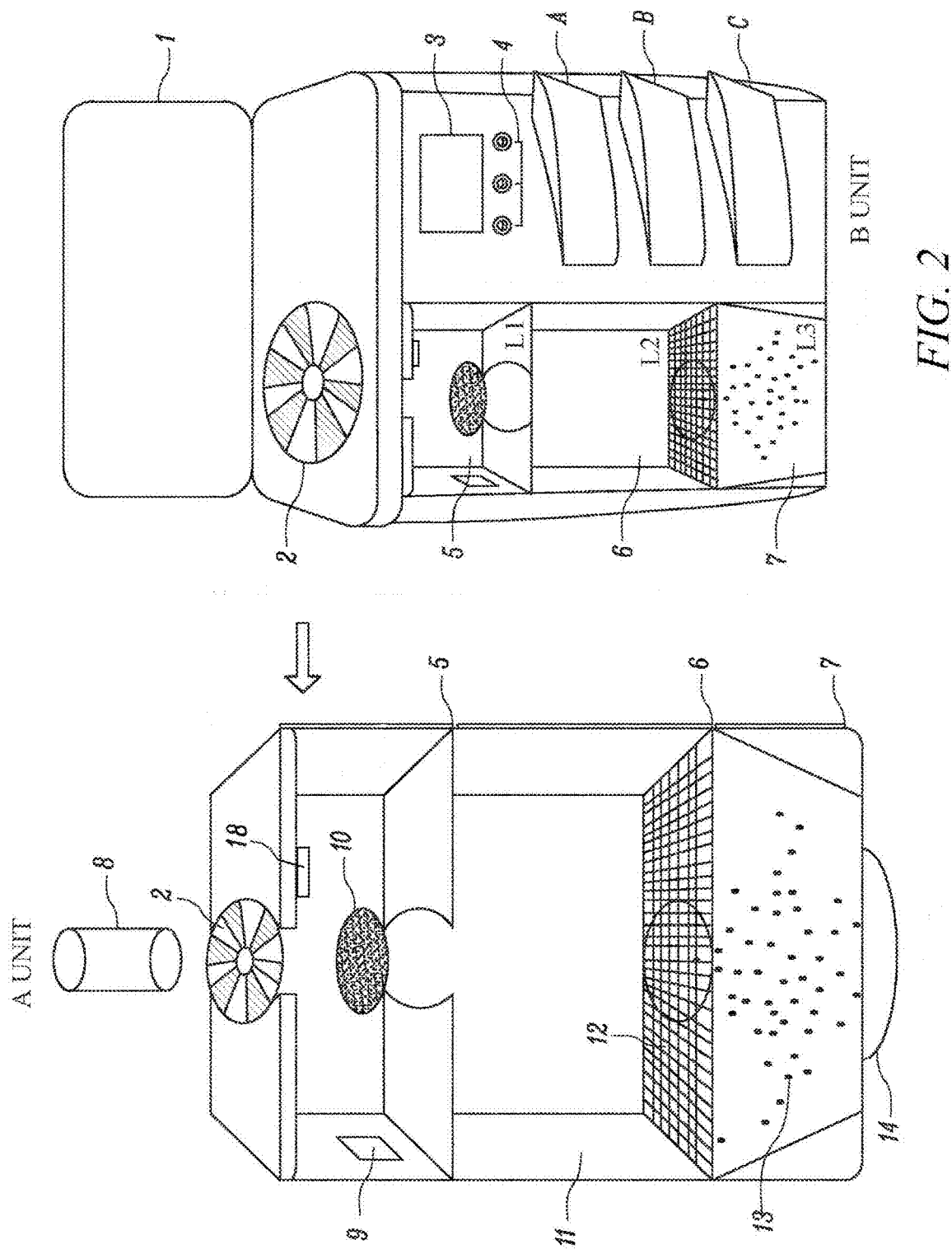
FIG. 2: The structure of the system including internal structure of the disposal unit. The partial view of the system showing internal structure of the disposal unit is included.
Figure 3:
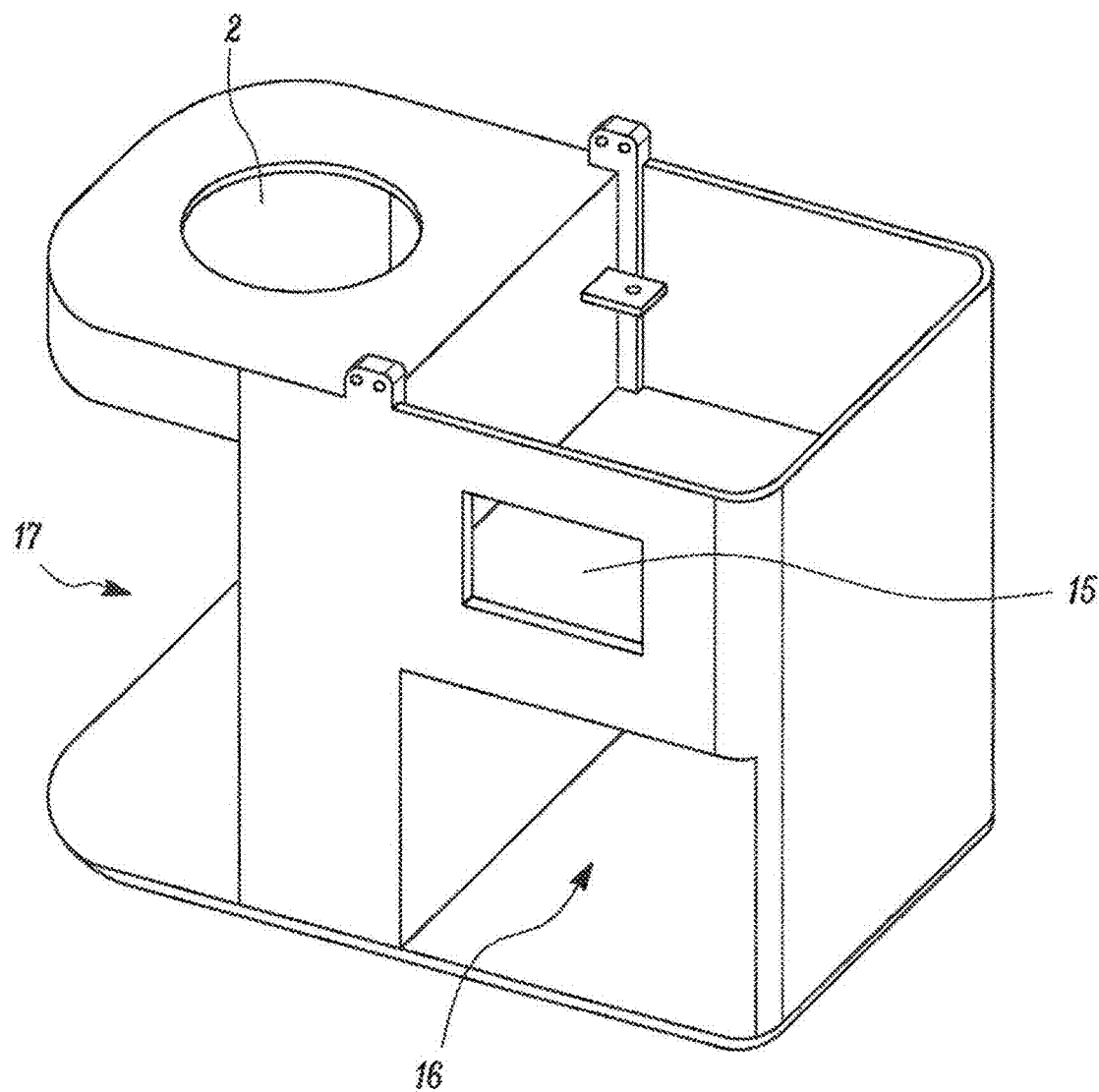
FIG. 3: A detailed view of the invention showing the front, side and top views of the invention.

According to various embodiments of the present invention described below, an interactive, compact and convenient system capable of dispensing and disposal of a sanitary material in a single unit is provided. Wherein the system is engineered in two modes. Namely, Firsts Mode & Second Mode. The First Mode offers a dual compartment disposal system. Whereas, the Second Mode offers a triple compartment disposal system. Disposals in both modes offer hygienic methods of disposing wastes involving minimal contact between the waste and person disposing the wastes. One of the most important embodiments of the invention is the interactive nature of the system which functions to detect the waste being deposited and offers to dispense a sanitary material in return. In one of the embodiments of present invention the body of the unit comprises of two parts: FIG. 1A, Unit A (left half): the disposal unit comprises of top surface and at least two compartments within the body. The top surface of the body located under the lid contains a 'securing cap' which upon being open allows the insertion of waste (8 of FIG. 1B) to be pushed into a first compartment L1, where the waste is temporarily collected until it advances into the below level L2. At least one sensor (18 of FIG. 1B, FIG. 2) is located around the opening at the 'securing cap', which identifies the waste as it passes through the opening.

FIG. 1A Unit B (right half): The top horizontal surface of Part B is plain and sealed. This part comprises of 3 storage drawers (A, B & C as marked in FIGS. 1A, 2, 4 & 5); Three buttons corresponding to the three storage drawers (such that button "A" opens drawer "A" etc.); and a display screen capable of showing short messages. The lowest drawer of the three drawers being the largest in size.

In one of the embodiments of the present invention, the interactive component of the invention involves at least one sensor that detects the waste being disposed and such detection is communicated to the display screen in the dispensing unit (FIG. 2,Unit B) of the system, and to the three storage drawers located in the dispensing unit. Such that drawer 'A' containing tampons would be unlocked when a used tampon is detected by the sensor(s) located in the disposing unit, and the display screen shows a message suggesting the preferred drawer/product located in the drawer, for example "for fresh tampons use drawer A".

The sensor 18 is selected from but not limited to an object detection sensor, a distance measuring sensor, IR sensors, optical sensors, laser sensors, or a combination thereof. In spite of the unlocked drawer and/or the message on display screen, the user has an option to avail any other kind of sanitary material located in any other drawer of the system.

In one of the embodiments of the present invention, the system is initiated using a payment system incorporating a coin collecting mechanism. Such that the lid of disposer and the drawers of the dispenser are accessible only on a payment of a certain pre-programmed amount.

Figure 4:
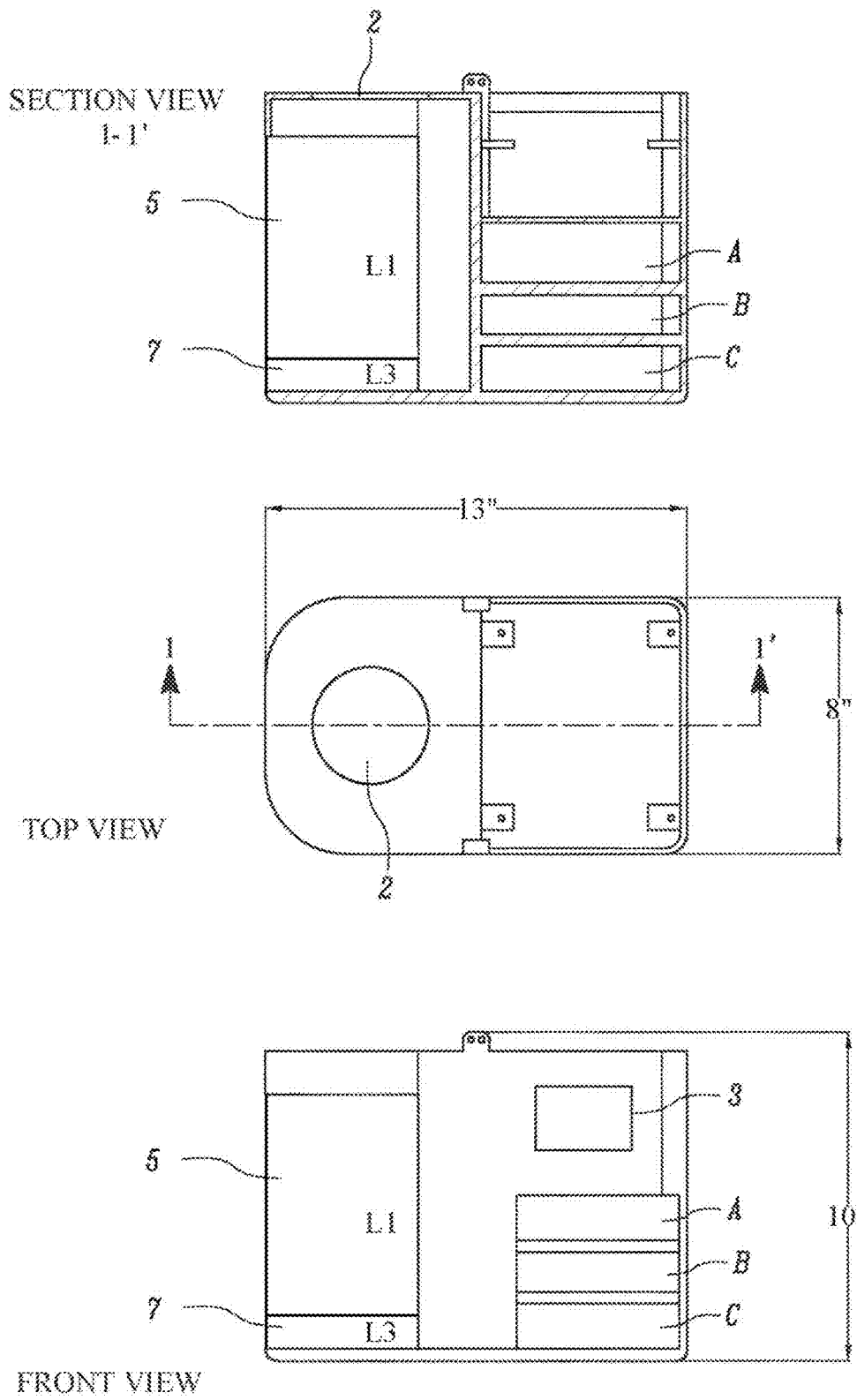
FIG. 4 A section view, a top view, and a front view of the invention. In this embodiment of the invention, there are two compartments in the disposal unit. Dimensions of the invention are shown.
Figure 5:
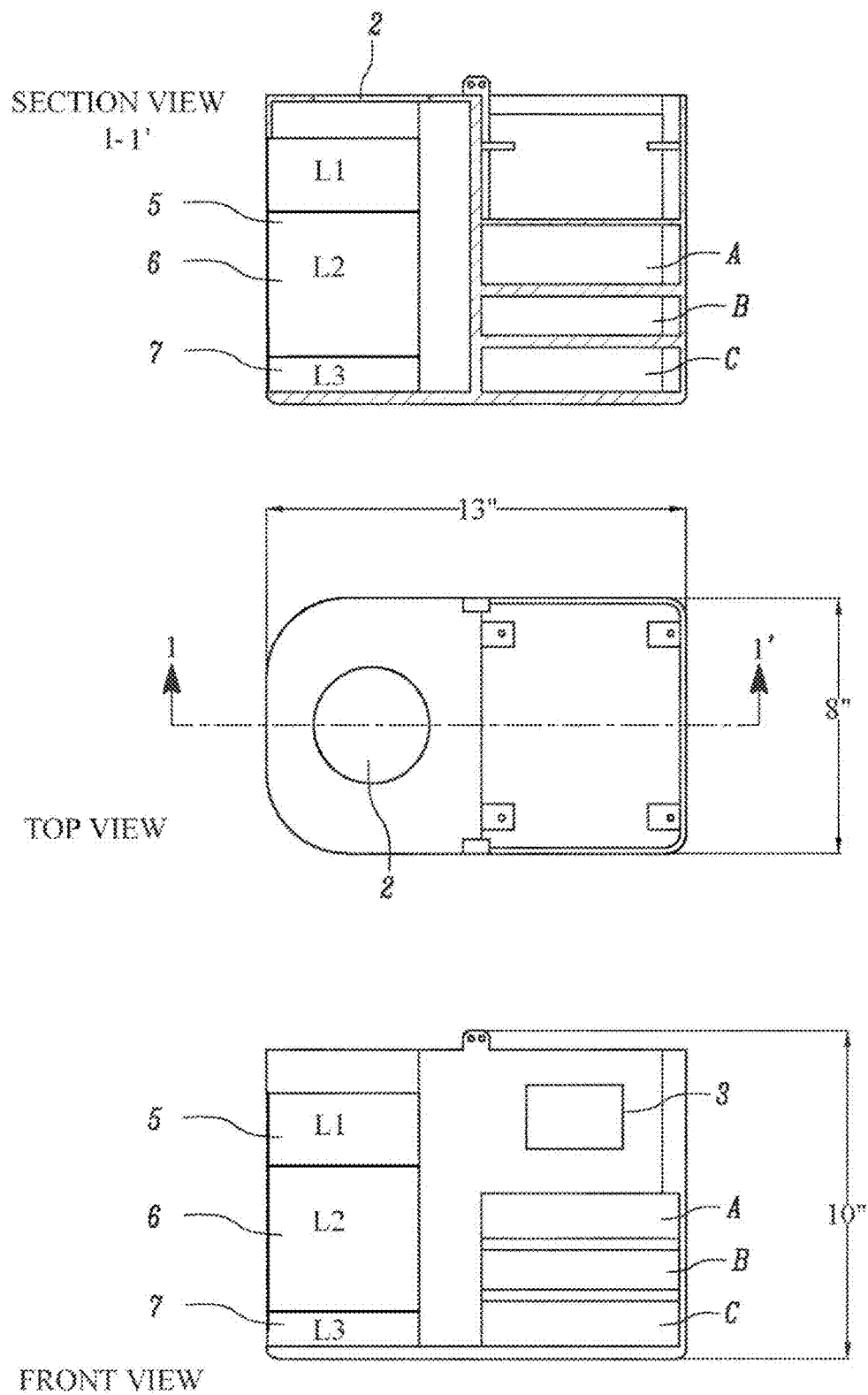
FIG. 5 A section view, a top view, and a front view of the invention. In this embodiment of the invention, there are three compartments in the disposal unit. The incinerator compartment is marked as L2. Dimensions of the invention are shown.

In one of the embodiments of the present invention, the body of the system has dimensions in the range of 13"-20": 8"-13": 10"-20" (Length:Width:Height) as seen in FIGS. 4 & 5. This concise and compact sizing allows the invention to be used in both public toilets (within the cabins) as well as private toilets (homes, offices, etc.) where such placement is necessary to maintain discretion of the usage.

In one of the embodiments of the present invention, the material used for the body of the system is selected from but not limited to fibers, resins used in medical applications, polyvinyl chloride (PVC), ($AlMg_7Si_3Mn$, $AlSi_{11}Cu_2Ni_2Mg_2Mn$), thermosets, thermoplastics, acrylic, HDP, Polyetheretherketone (PEEK), Polypropylene (PP), Polyethylene (PE), Polystyrene (PS), Nylon, Polyethylene terephthalate (PET), Polyamide (PA), acrylonitrile butadiene (ABS), Polyurethane (PU), or a combination thereof. Materials that are heat-resistant and antibacterial in nature are most suitable to maintain the hygiene levels of the invention while ensuring its durability.

In one of the embodiments of the present invention, the dispensing compartment comprises of three drawers. The bottom most drawer being the largest of the three drawers. Such drawers have a capacity to store at a time, at least 6-25 tampons, sanitary napkins, other hygiene products, or a combination thereof.

In one of the embodiments of the present invention, the dispensing compartment comprises of at least one display screen placed above the three dispensing drawers. The display screen is optionally connected to three buttons present directly below the screen. Each button represents a dispensing drawer, such that on pressing a button the respective drawer opens. Such mechanism is optionally connected to the display screen that displays a message on pressing a button.

In one of the embodiments of the present invention, the sensor(s) of the disposal unit are connected to the display screen in the dispensing compartment. Such that when a waste passes through the sensors the information is communicated to the display screen which in turn displays a message. Additionally, the sensor(s) is connected to the three drawers located in the dispensing unit. Such that when a waste passes through the sensors, said waste is identified and corresponding drawer containing fresh product same/similar to the waste product is unlocked/offered to the user.

In one of the embodiments of the present invention, compartments of the invention contain at least a disinfecting agent, a fragrant agent, an odorant, an antibacterial agent, an anti-fungal agent, a dehumidifying agent, or a combination thereof. L1 represents the presence of such elements in a small square marked on its left wall (9 of FIG. 1B).

In an embodiment of the present invention, the disposal system using the first mode of disposal, comprises of two compartments, a receiving compartment and a collective compartment. The receiving compartment temporarily receives the waste before the waste falls into the collective compartment. The collective compartment is a drawer which can be detached from the main system, emptied of its contents and retracted into the system.

In an embodiment of the present invention the collective compartment of the first mode is lined with a plastic bag. The waste received by the collective compartment falls into the bag and once the compartment is full, the compartment is drawn open, the bag containing the waste is collected and replaced by a fresh empty bag before the compartment is retracted or closed into the system.

In one of the embodiments of the present invention, once the waste enters through the disposal compartment, the sensor(s) (18 of FIG. 1B, FIG. 2) measure the dimension(s) of the waste and communicate the information to the display screen, based on which information, the user is offered to select the preferred product from the dispenser, and the relevant drawer located in the dispensing unit is unlocked. Once the waste enters into the receiving compartment of the First Mode, it passes into the collective compartment below. Preferably, after nine cycles completed by the system, the collecting drawer is opened and emptied.

In another embodiment of the present invention the disposal system using the second mode of disposal, comprises of three compartments, a receiving compartment, an incinerating compartment and a collective compartment. The receiving compartment temporarily receives the waste before the waste falls into the incinerating compartment. The incinerating compartment functions to reduce the waste volume, partly disinfect waste, completely disinfect waste or a combination thereof. The floor of the incinerating compartment is an electric mesh (12 of FIG. 1B), through which the ashes (13 of FIG. 1B) falls into the collective compartment. Alternatively, the floor of the incinerator compartment opens in a manner allowing the waste to fall into the collective compartment. The collective compartment is a drawer which can be detached from the main system, emptied of its contents and retracted into the system. Alternatively, the collective compartment has an opening in its floor (14 of FIG. 1B) through which the waste is exited. L2 is the incinerator level. The floor of this level comprises of an electric mesh, the walls of the level are coated with charcoal or such other absorbing element (it will absorb the fumes generated by the incineration) (11 of FIG. 1B). Optionally, the walls of L2 may include means for ventilation, such as apertures (e.g., slits, holes, slots, and vents) or an exhaust. L3 is the last level which collects the incinerated waste ready to be disposed. The walls of L3 are slightly angled to direct the reduced waste into the floor of L3 which comprises of a collection bag, or a connected pipe or such other disposing mechanism. Optionally, the waste material is not fully incinerated before being collected by a collection bag, a connected pipe or such other disposing mechanism.

In an embodiment of the present invention, the waste received by the collective compartment falls into the bag and once the compartment is full, the compartment is drawn open, the bag containing the incinerated waste is collected and replaced by a fresh empty bag before the compartment is retracted or closed into the system.

In one of the embodiments of the present invention, once the waste enters through the disposal compartment, the sensors calculate the dimension(s) of the waste and communicate the information to the display screen, which prompts the user to select the preferred product from the dispenser and additionally unlocks the drawer containing the preferred product. Once waste enters into the receiving compartment of the second mode, it passes into the incinerating compartment containing an electric mesh floor.

In one of the embodiments of the present invention, once the waste passes through the receiving compartment, the roof of the incinerating compartment labeled as 'opening flap' (10 of FIG. 1B) closes until the incineration process is complete. The incineration process is initiated when the waste comes in contact with the electric mesh or when it is initiated by the user. Once the incineration process is complete, the waste products or ashes fall through the mesh into the collective compartment where they are stored until disposed of.

In one of the embodiments of the present invention, the disposal compartments of the Second Mode is made using thermo-resistant materials selected from but not limited to corrosion resistant metals such as stainless steel, various alloys or ceramics; insulating materials such as fiber glass asbestos; graphene oxide and its composites; biomaterials; Polymers such as Polypropylene (PP), Polyethylene (PE), Polyvinyl Chloride (PVC), Polycarbonate, Polyether ether ketone (PEEK), duroplast, Polypropylene, Polypropylene (PP), Polyethylene (PE), Polystyrene (PS), Nylon, Polyethylene terephthalate (PET), Polyamide (PA), Polycarbonate (PC), Acrylonitrile butadiene styrene (ABS), Polyurethane (PU), or a combination thereof. Preferably, thermosets are used.

In one of the embodiments of the present invention, the incinerating compartment of the second mode uses an electric mesh, including but not limited to an electrically powered heating coil, an electrical resistance coil, or such other form which operates at 110/220 VAC or electric power at a frequency of 60 Hz/50 Hz.

In one of the embodiments of the present invention, the second mode contains at least a vent, an absorbent, an exhaust pipe, or a combination thereof. Such vent may use a fan system or such other mechanism to exude any gas, smoke dust, or other substances. The absorbent may be selected from but not limited to air filet such as carbon filter, toxic gas filter inter alia. The absorbent used may be replaceable if required.

In yet another embodiment of the present invention, a hygienic interactive system for sanitary material comprises a dispenser and a disposal; wherein the disposal comprises an incinerator is presented, wherein the hygienic interactive system for sanitary material further comprises at least one sensor, wherein the at least one sensor detects a disposed waste item and determines a suitable sanitary material for dispensing.

USEFUL FEATURES OF THE INVENTION

The present invention is compact and can be placed in home toilets as well as public toilets (within the cabins).

The present invention also increases the hygiene level of both handling sanitary waste and using sanitary materials.

The present invention provides an interaction unique to this market (dispenser/disposer) thereby advancing presently available inventions using an incineration technique for home use by individuals without requirement of skill or training to operate it, is yet another achievement of this invention as accommodating an incinerator within small spaces without any assistance of a trained person is an advancement in this market especially since it addresses the primary problem of sanitary waste disposal in the most hygienic manner possible.

The present invention optionally offers an intelligent sensing system which identifies the user's choice of sanitary material and offers fresh material accordingly. The present invention also offers the most hygienic and convenient solution to the existing problem faced during menorrhea. It eliminates the problem of 'waste handling', 'waste disposal' as well as 'sanitary material storage' and 'sanitary material dispensing'

The following examples illustrate the invention but do not limit the scope of the invention:

Example 1

Rolled and used sanitary napkin (size XL) was passed through the securing cap into L1. The waste fell through L1, into L3. As the waste passed through the securing cap, the sensors detected the waste, the display screen projected "Fresh XL sanitary napkins available in drawer C' and Drawer C was automatically unlocked. The used waste was collected from L3.

Example 2

A used tampon was passed through the securing cap into L1. The waste fell through into L2. As the waste passed through the securing cap, the sensors detected the waste, the display screen projected "Fresh sanitary napkins available in drawer A' and Drawer A was automatically unlocked. The used waste was incinerated in L2, incinerated waste fell into L3 and was collected at the end of the cycle.

I claim:

1. A hygienic interactive system for sanitary material operable to identity of material being disposed and consequently operable to offer to dispense a replacement material comprising:
a dispenser unit having a display screen and at least three drawers; said display screen being accessible from an outer body of said dispenser unit;
a disposal unit having at least two compartments being connected with said dispenser unit;
said disposal unit having a waste receiving compartment and a waste collecting compartment;
said waste receiving compartment having at least one sensor operable to identify deposited material;
said sensor being operably connected with said display screen and with said drawers of said dispenser;
said system operable to communicate to the said screen a location of a said dispenser drawer containing a replacement material; said system being operable to automatically unlock said dispenser drawer containing said replacement material.

2. The hygienic interactive system for sanitary material of claim 1, wherein said system has dimensions in the range of 13"-20": 8"-13": 10"-20" (Length: Width: Height); storage capacity of at least nine fresh tampons, at least nine fresh sanitary napkins, and at least nine used sanitary material at once.

3. The hygienic interactive system for sanitary material of claim 1, wherein said disposal unit comprises:
a hygiene enhancing agent selected from but not limited to a disinfecting agent, a fragrant agent, an antibacterial agent, an anti-fungal agent, a dehumidifying agent, or combinations thereof.

4. A hygienic interactive system for sanitary material operable to identity of material being disposed and consequently operable to offer to dispense a replacement material comprising:
a dispenser unit having a display screen and at least three drawers; said display screen being accessible from an outer body of said dispenser unit;
a disposal unit being connected with said dispenser unit;
said disposal unit having a waste receiving compartment, an incinerating compartment and a waste collecting compartment;
said waste receiving compartment having at least one sensor operable to identify deposited material;
said sensor being operably connected with said display screen and with said drawers of said dispenser;
said system operable to communicate to the said screen a location of a said dispenser drawer containing a replacement material; said system being operable to automatically unlock said dispenser drawer containing said replacement material.

5. The hygienic interactive system for sanitary material of claim 4, wherein said incinerating compartment comprises a floor; a vent; an absorbent; and, optionally an exhaust pipe; wherein the floor comprises an electric mesh selected from the group consisting of an electrically powered heating coil, an electrical resistance coil, or combinations thereof.

6. The hygienic interactive system for sanitary material of claim 5, wherein said floor is configured to allow waste to fall into a collective compartment.

7. The hygienic interactive system for sanitary material of claim 4, wherein said system has dimensions in the range of 13"-20": 8"-13": 10"-20" (Length: Width: Height); storage capacity of at least 9 fresh tampons, at least nine fresh sanitary napkins, and at least fifteen used sanitary material at once.

8. The hygienic interactive system of claim 1 wherein said hygienic interactive system is made of material selected from a group consisting of polyvinyl chloride (PVC), $AlMg_7Si_3Mn$, $AlSi_{11}Cu_2Ni_2Mg_2Mn$, thermoplastics, thermosets, acrylics, HDP, polyether ether ketone (PEEK), polypropylene (PP), polyethylene (PE), polystyrene (PS), nylon, polyethylene terephthalate (PET), polyamide (PA), acrylonitrile butadiene styrene (ABS), polyurethane (PU), or combinations thereof.

9. The hygienic interactive system of claim 4 wherein said system is made of material selected from a group consisting of polyvinyl chloride (PVC), $AlMg_7Si_3Mn$, $AlSi_{11}Cu_2Ni_2Mg_2Mn$, thermoplastics, thermosets, acrylics, HD, polyether ether ketone (PEEK), polypropylene (PP), polyethylene (PE), polystyrene (PS), nylon, polyethylene terephthalate (PET), polyamide (PA), acrylonitrile butadiene styrene (ABS), polyurethane (PU), or combinations thereof.

10. The hygienic interactive system for sanitary material of claim 1, wherein said disposal sensor is selected from an object detection sensor, IR sensor, laser sensor, or combinations thereof.

11. The hygienic interactive system for sanitary material of claim 4, wherein said disposal sensor is selected from an object detection sensor, IR sensor, laser sensor, or combinations thereof.

12. The hygienic interactive system for sanitary material of claim 4, wherein said disposal unit comprises a hygiene enhancing agent selected from but not limited to a disinfecting agent, a fragrant agent, an antibacterial agent, an anti-fungal agent, a dehumidifying agent, or combinations thereof.

* * * * *